United States Patent [19]

Choi

[11] Patent Number: 5,003,962
[45] Date of Patent: Apr. 2, 1991

[54] LARYNGOSCOPE WITH DOUBLE-ANGLE BLADE

[76] Inventor: Jay J. Choi, 7 Moran Rd., West Orange, N.J. 07052

[21] Appl. No.: 560,218

[22] Filed: Jul. 26, 1990

Related U.S. Application Data

[63] Continuation of Ser. No. 349,836, May 10, 1989, abandoned.

[51] Int. Cl.$^5$ ............................................. A61B 1/06
[52] U.S. Cl. ..................................... 128/11; 128/10
[58] Field of Search ..................... 128/10, 11, 207.14, 128/200.26

[56] References Cited

U.S. PATENT DOCUMENTS

| | | | |
|---|---|---|---|
| 3,643,654 | 2/1972 | Felberg | 128/11 |
| 3,943,920 | 3/1976 | Kandel | 128/11 |
| 4,114,609 | 9/1977 | Moses | 128/11 |
| 4,360,008 | 11/1982 | Corazzelli, Jr. | 128/11 |

FOREIGN PATENT DOCUMENTS 2728910  1/1978  Fed. Rep. of Germany ........ 128/11

OTHER PUBLICATIONS

Anesthesiology-The Journal of the American Society of Anesthesiologists, Inc., vol. 17, 1956, pp. 38–42.
Clinical Reports—An Angulated Laryngoscope for Routine and Difficult Tracheal Intubation, C. P. Bellhouse, pp. 126–129.
Endotracheal Intubulation: A New Blade for Direct Laryngoscopy, Otto C. Phillips, M.D., Roger L. Duerksen, M.D., pp. 691–698.

*Primary Examiner*—Edward M. Coven
*Assistant Examiner*—Mark S. Graham
*Attorney, Agent, or Firm*—Mathews, Woodbridge and Collins

[57] ABSTRACT

This invention relates to a laryngoscope with an improved double-angle blade or spatula which has three segments lengthwise. The first segment extends in a direction substantially normal to the handle to a first bend, at which the blade or spatula is bent toward the handle through an angle of 20 degrees. The second segment extends in a new direction to a second bend inward through an angle of 30 degrees, forming a third segment which extends to the distal tip. A small cylindrical bulb is superposed adjacent to and parallel to the top edge, near the end of the second segment. This is energized by batteries in the handle.

5 Claims, 3 Drawing Sheets

LARYNGOSCOPE WITH DOUBLE-ANGLE BLADE

This is a continuation of Ser. No. 349,836, filed May 10, 1989, abandoned.

BACKGROUND OF THE INVENTION

This relates in general to techniques for endotracheal intubation known as laryngoscopy, and more particularly, to instruments for performing laryngoscopy known as laryngoscopes.

The use of laryngoscopy for placing a tube in the trachea has been practiced since the end of the last century. Since that time, the search for improved methods and instruments for intubation has continued.

An early laryngoscope developed by C. Jackson had a U-shape. In 1913, Janeway designed an L-shaped instrument with a blade having a slight curve at the end, and with batteries in the handle. In 1941 R. A. Miller described a laryngoscope blade with a smaller tip than those commonly used at the time, and with a curve which began about two inches from the end. In 1943, R. R. McIntosh developed a blade curved along its entire length. In 1973, a blade was developed by O. C. Phillips which combined the curved tip of Miller and the shaft of the Jackson blade. More recently, in 1988, C. P. Bellhouse developed an angulated laryngoscope which includes essentially a straight blade modified by bending forward through 45 degrees at the midpoint. Because the angle of this blade may obscure the view of the entire larynx, a flange is provided to enable a prism to be fitted flush to the laryngoscope blade to enable the user to see around the corner. However, this makes less room available for intubation, and increases the potential for damage to the teeth.

Still today, there are patients for whom intubation is either difficult or impossible with available techniques.

Accordingly, it is the principal object of this invention to develop an improved blade or spatula that makes both visualization of the larynx and intubation possible in the most difficult cases and for the widest spectrum of patients.

Another object is to provide a blade or spatula which is incrementally curved to lift the epiglottis and reduce the need to tilt the laryngoscope posteriorly.

Still another object is to provide a blade or spatula which has a wide flat surface to allow easy handling of the tongue and epiglottis.

Another object of the invention is to provide a laryngoscope which is easy to handle and to clean.

These and other objects are achieved in a laryngoscope having a double-angle blade or spatula. In a preferred embodiment, the latter blade is 3 millimeters thick, 2½ centimeters wide at its proximal end which is coupled to the handle. The blade or spatula has three segments lengthwise. The first segment extends in a direction substantially normal to the handle to a first bend, at which the blade or spatula is bent inward toward the handle through an angle of 20 degrees. This forms a second segment which extends 5.4 centimeters in a new direction to a second bend inward through an angle of 30 degrees, forming a third segment which extends 2.6 centimeters to the distal tip.

A particular feature of the laryngoscope of the present invention is a small cylindrical bulb superposed adjacent and parallel to the top edge near the end of the second segment. This is connected by a wire or optical fiber running along the side of the blade or spatula to the handle, where batteries are stored.

Particular advantages of the double-angle laryngoscope of the present invention is that:

(a) it allows more room for intubation;

(b) it decreases potential for damage to the Patient's teeth;

because the spatula or blade has two incremental curvatures;

(c) it improves lifting of the epiglottis;

(d) it reduces the need for the operator to tilt the laryngoscope posteriorly during the procedure;

because the spatula or blade has a wide and flat surface;

(e) it allows easy handling of a big tongue nd epiglottis;

because of its simplicity;

(f) the laryngoscope of the present invention is easy to handle and easy to clean.

Other objects, features and advantages of this invention will be better understood from a detailed study of the specification and claims hereinafter with reference to the attached drawings.

SHORT DESCRIPTION OF THE DRAWINGS

DETAILED DESCRIPTION OF THE INVENTION

Figure 1:
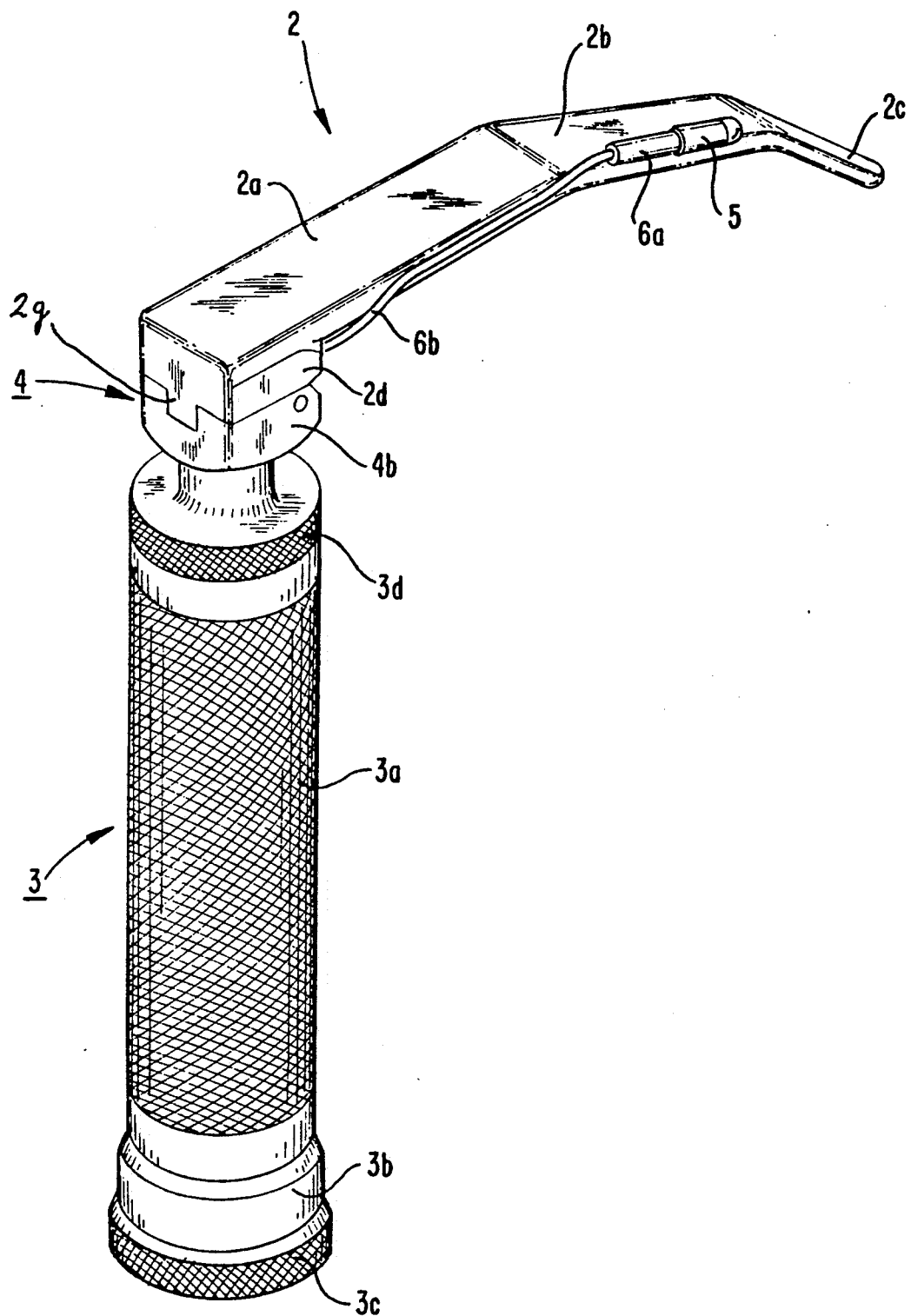
FIG. 1 is a perspective showing of the double-angle laryngoscope of the present invention.
Figure 3:
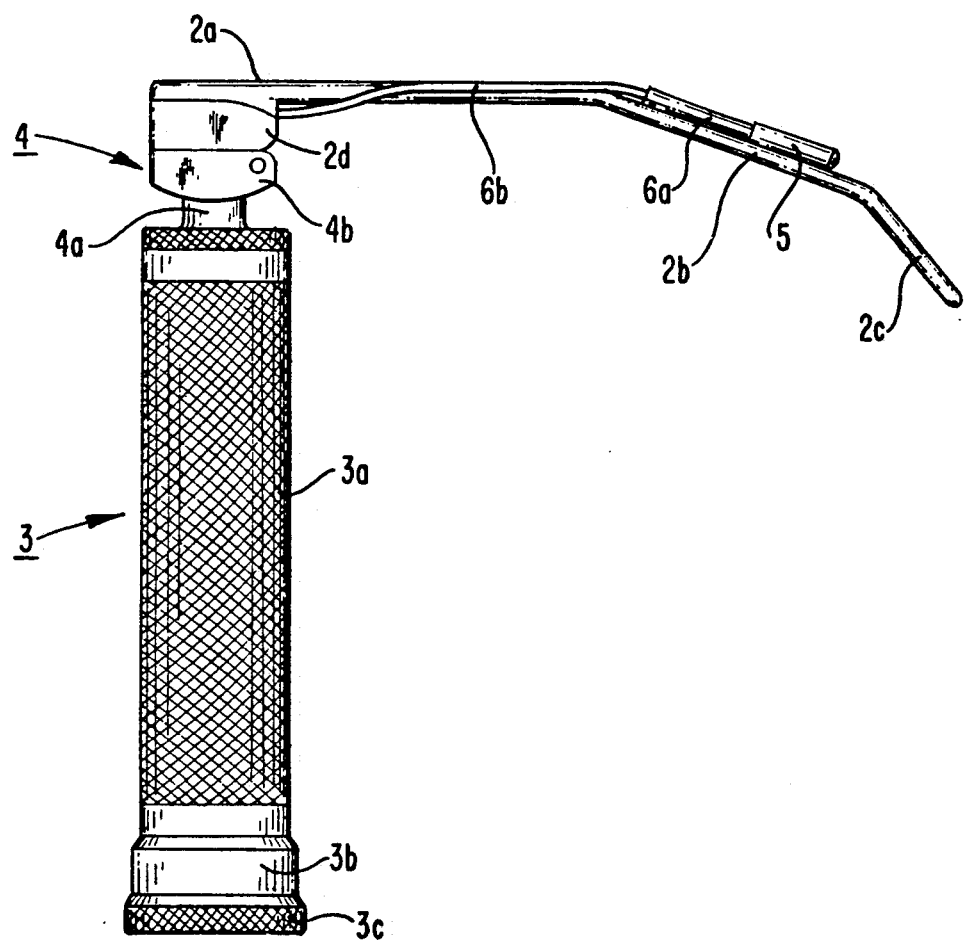
FIG. 3 is a side-elevational showing of the laryngoscope of FIG. 1.

Referring to FIG. 1 of the drawings, there is shown, in preferred form, the laryngoscope 1 with the double-angled blade or spatula 2 of the present invention, the proximal end of which is mounted in substantially normal relation to the principal axis of a cylindrical handle 3.

Figure 2:
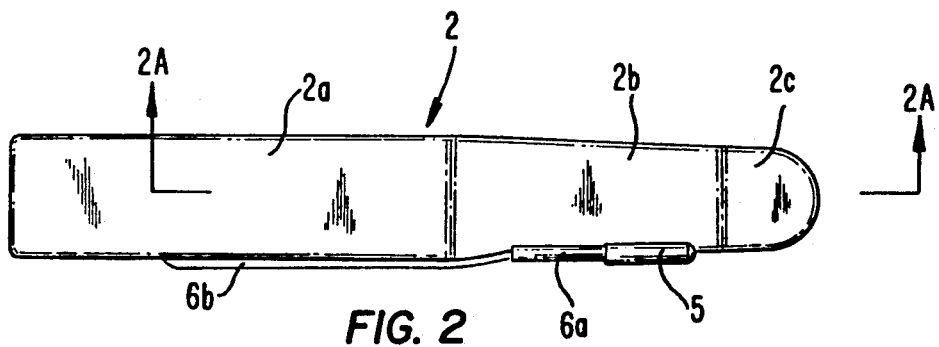
FIG. 2 is a top-elevational view of the laryngoscope of FIG. 1, showing the blade or spatula.
Figure 2A:
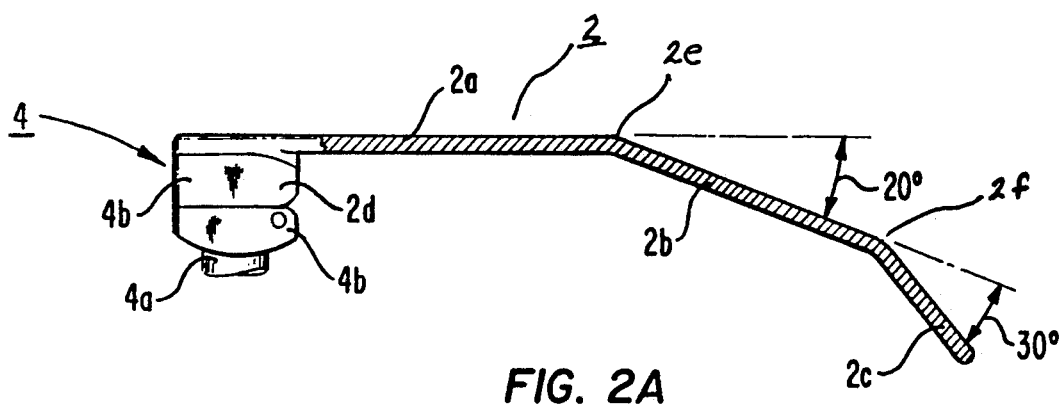
FIG. 2A is a section through the plane indicated by the arrows 2A—2A of FIG. 2, in which the angles of the bends in the blade or spatula are indicated.
Figure 4:
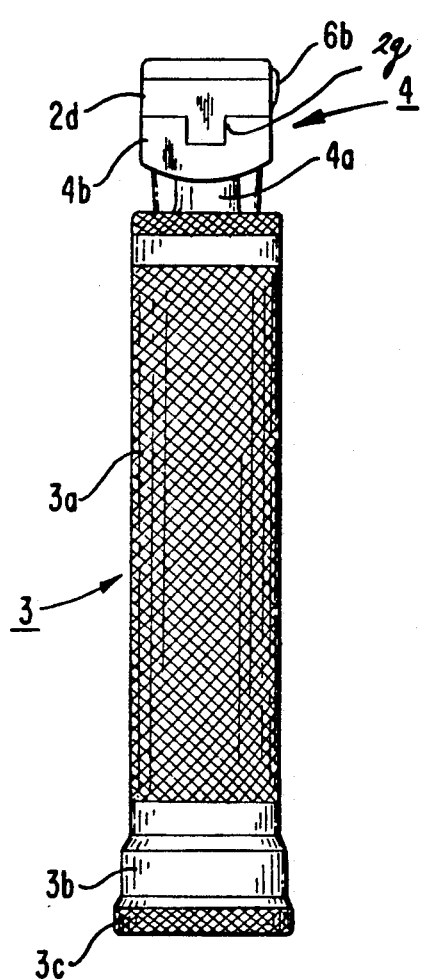
FIG. 4 is a left-side elevational view of the laryngoscope of FIG. 1.
Figure 5:
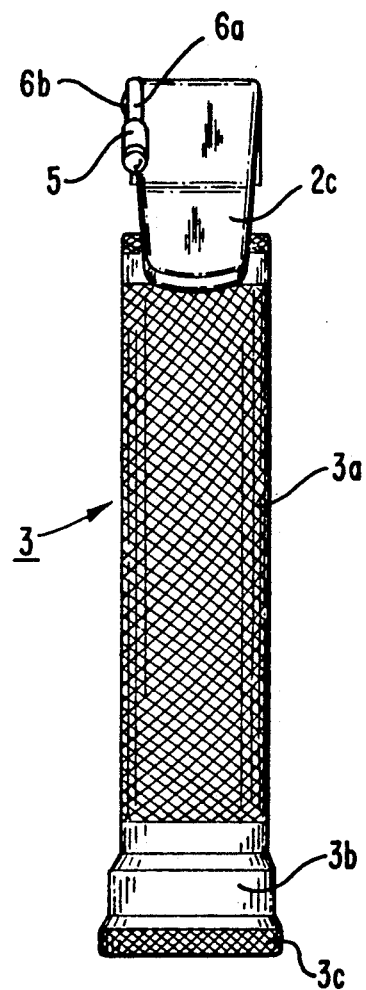
FIG. 5 is a right-side elevational view of the laryngoscope of FIG. 1.

The blade 2, in preferred form, is essentially a straight blade of stainless steel, in the form of a spatula, 3 millimeters (0.1181 inch) thick and 16 centimeters (6.299 inches) in overall length, which is divided into three sections, 2a, 2b, and 2c by two inward angular bends 2e and 2f. (See FIG. 2A). The first section 2a extends 8 centimeters (3.15 inches) from the proximal end attached to the handle 3, and in a direction normal to the principal axis of the handle 3, to the first bend 2e, which extends across the width of the blade 2. Section 2b forms, with the original direction of 2a, an angle of 20 degrees, extending 5.4 centimeters (2.126 inches) in a new direction to a second bend 2f across the width, as shown in FIG. 2A. This forms an angle of 30 degrees between the ordinal direction of 2b and the distal or tip section 2c of the blade 2. The latter extends 2.6 centimeters (1.024 inches) from the bend 2f terminating in a rounded end.

The proximal end of section 2a terminates in a downwardly-extending shank 2 d of rectangular cross-section, approximately 2.5 centimeters (0.984 inch) in width, and extending down 1.8 centimeters (0.73 inches) from the surface of 2a, including a central rectangular projection 2g which runs across the width of 2d in the direction of the principal axis of the blade 2. The projection 2g keys into and mates with a matching slot 4c in the rectangular yoke 4b of coupling 4. The yoke 4b may be of similar length and width to the shank 2d, and have a thickness of, say 4 millimeters (0.157 inch), for mounting the blade 2 with conventional screw fittings on the handle 3. The yoke 4a is centered on a cylindrical collar 4a, which has an outer diameter of, say, 2 centimeters (0.787 inch), and is mounted in coaxial relation to the long axis of the handle 3.

In the present embodiment, the handle 3 may comprise, for example, a barrel 3a having a knurled outer surface 14.61 centimeters (5.75 inches) long, and 5.72 centimeters (2.25 inches) in outer diameter, terminating at its lower end in a pair of annular flanges 3b and 3c of slightly larger diameter to facilitate grasping and holding. The handle 3 is hollow, serving as a housing for batteries to empower the light source 5. The latter may comprise a small cylindrical bulb (2.5 Volt, 0.28 ampere), say 3.18 centimeters (1.25 inches) long and 0.48 centimeters (0.188 inches) in diameter, which is disposed parallel to the lateral edge on the left-hand side of segment 2b of the blade or spatula 2, so that its central axis is substantially aligned with the edge. The tip of the bulb 5 is located, say, about 1 centimeter (0.3937 inch) behind the second bend 2f. The bulb 5 has a focal length of say, 2 centimeters (0.7874 inch) so that the light therefrom is focused on the center of the tip of section 2c of the blade or spatula 2.

The bulb 5 screws into or is otherwise secured in electrical contacting relation to a cylindrical socket 6a which is also aligned with the edge of blade section 2b. The socket 6a is connected by a fine wire or fiberglass connecting filament 6b which runs along and is secured to the edge of the blade 2, passing into the shank 2d, where it passes into the handle 3 through the coupling 4, and is connected to conventional batteries contained therein.

The laryngoscope of the present invention is grasped by the user, the blade or spatula 2 being inserted from the right corner of the mouth, in the groove between the right tonsil and the tongue. Care is taken to hold the tongue to the left, and to avoid levering the blade 2 on the upper teeth. Because of the double angulation of the blade or spatula 2, visibility of the larynx is increased, while the risk of pressure on the upper teeth is reduced.

This double-angle blade or spatula 2 provides an innovative advancement in the field of anesthesiology.

It will be understood that the invention is not limited to an instrument of the specific form or dimensions disclosed herein by way of example, but only by the scope of the appended claims.

What I claim is:

1. A laryngoscope for tracheal intubation which comprises in combination:
   a handle;
   a blade the proximal end of which is coupled so that it extends outward L-fashion from the end of the handle, said blade of substantially flat solid section being shaped in the form of a spatula having a tip, being bent inwardly through a first and second bend toward the principal axis of the handle, forming at least two acute angles in said spatula along the length between the coupling with the handle and the tip so that the extent of the blade or spatula is divided into at least three relatively straight sections, angled inwardly toward one another and
   wherein said first bend is formed on said spatula about halfway between its proximal end and its tip, and said second bend is formed more than two-thirds of the distance from said first bend to said tip.

2. The combination in accordance with claim 1 wherein each of said acute angles between the said sections do not exceed about 30 degrees.

3. The combination in accordance with claim 1 wherein said first bend forms an acute angle approximately 20 degrees with the preceding section, and said second bend forms an acute angle approximating 30 degrees with the preceding section.

4. The combination in accordance with claim 1 comprising lighting means in the form of a cylindrical bulb disposed with its long axis substantially parallel to and projecting slightly beyond a lateral edge of said spatula, and focused on said tip.

5. A subcombination blade for use in a laryngoscope comprising a handle and blade, said blade having a proximal end which is adapted to be coupled to the handle so that it extends outward L-fashion from an end of the handle, said blade being shaped in the form of a spatula having a tip, being bent inwardly through a first and second bend toward the principal axis of the handle, forming at least two acute angles in said spatula along the length between the coupling with the handle and the tip so that the extent of the blade is divided into at last three relatively straight sections, angled inwardly toward one another and
   wherein said first bend is formed on said spatula about halfway between its proximal end and its tip, and said second bend is formed more than two-thirds of the distance from said first bend to said tip.

* * * * *